United States Patent [19]

Lui et al.

[11] Patent Number: 5,646,329

[45] Date of Patent: Jul. 8, 1997

[54] CYCLOPROPYLAMINE DERIVATIVES

[75] Inventors: Norbert Lui, Köln; Albrecht Marhold, Leverkusen; Stefan Böhm, Krefeld, all of Germany

[73] Assignee: Bayer Aktiengesellschaft, Leverkusen, Germany

[21] Appl. No.: 554,325

[22] Filed: Nov. 2, 1995

[30] Foreign Application Priority Data

Nov. 9, 1994 [DE] Germany .......................... 44 40 021.7

[51] Int. Cl.[6] .................................................. C07C 305/00
[52] U.S. Cl. .......................... 560/27; 564/168; 564/183; 564/185; 564/218; 564/219
[58] Field of Search ........................... 560/27; 564/168, 564/185, 183, 218, 219

[56] References Cited

PUBLICATIONS

K.R. Gassen, et al., Journal of Fluorine Chemistry, vol. 49, pp. 127–139, (1990).
O. Tamura, et al., Tetrahedron, vol. 50, No. 13, pp. 3889–3904, (1994).

*Primary Examiner*—Michael L. Shippen
*Attorney, Agent, or Firm*—Sprung Horn Kramer & Woods

[57] ABSTRACT

2-fluoro-cyclopropylamine is prepared in an advantageous manner by reacting an N-vinyl compound with a carbene of type FXC: (where X=chlorine or bromine) to give the corresponding cyclopropylamine derivative, replacing the radical X in this derivative by hydrogen, by reduction, and finally eliminating the other substituents on the hydrogen atom.

3 Claims, No Drawings

CYCLOPROPYLAMINE DERIVATIVES

The present invention relates to a particular advantageous process for the preparation of 2-fluorocyclopropylamine from N-vinyl compounds and to novel cyclopropylamine derivatives which are obtained as intermediates in this process.

There are already two known ways of preparing of 2-fluorocyclopropylamine. One involves starting from butadiene, which is converted with a fluorohalogenocarbene halogeno-carbene into a vinylhalogenocyclopropane derivative, from which the 2-fluorocyclopropylamine is obtained by way of the following stages: oxidation to the carboxylic acid, reductive removal of the halogen atom, conversion to the acid chloride, reaction with an azide to the corresponding isocyanate, and hydrolysis of the latter (see J. Fluorine Chem. 49, 12–139 1990)). In addition to the multi-stage nature of this process, other disadvantages include the problematic accessibility and handling of the required azide and the low yield in some of the component steps. For instance, the yield in the reaction with the carbene is only 31%, and in the reductive removal of the halogen atom is only 10%. In the overall process, 2-fluorocyclopropylamine is obtained in a yield of less than 3%.

The second way involves reacting N-benzyl-N-vinyl-carbamate with the carbene HFC: and eliminating the benzyl group and the carbamate group from the reaction product (see Tetrahedron 50, (13) 3889–3904 (1994)). $CHFJ_2$, the precursor of the carbene HFC:, has to be prepared in a plurality of stages from various reagents (potassium iodide, antimony(III) fluoride, tribromomethane) and, for conversion to HFC:, brought into contact with the self-igniting diethylzinc. This process is too complex and too expensive to be employed on the industrial scale.

Thus there continues to be a need for a less complicated process for preparing 2-fluorocyclopropylamine, which can be carried out even on the industrial scale and achieves good yields.

A process for the preparation of 2-fluorocyclopropylamine has now been found which is characterized in that an N-vinyl compound of the formula

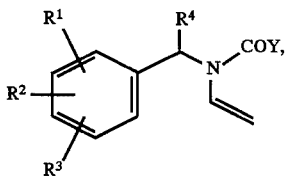

in which $R^1$, $R^2$ and $R^3$ independently of one another in each case represent hydrogen, $C_1$–$C_6$-alkyl, halogen, $C_1$–$C_6$-halogenoalkyl or $C_1$–$C_6$-alkoxy, $R^4$ represents hydrogen, $C_1$–$C_6$-alkyl or $C_6$–$C_{12}$-aryl, and Y represents open-chain or cyclic $C_1$–$C_{12}$-alkoxy, $C_6$–$C_{12}$-aryl, $C_7$–$C_{12}$-aralkyl, $C_7$–$C_{12}$-aralkyloxy or open-chain or cyclic $C_1$–$C_{12}$-alkyl, is reacted with a carbene of type FXC:, where X=chlorine or bromine, to give a cyclopropylamine derivative of the formula (II)

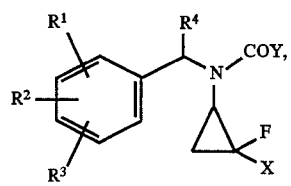

in which $R^1$, $R^2$, $R^3$, $R^4$, X and Y are as defined above,

X is replaced by hydrogen in the cyclopropylamine derivative of the formula (II), by reduction, and finally the COY group and the substituted or unsubstituted benzyl group are eliminated from the nitrogen atom.

Where $R^1$, $R^2$ and $R^3$ denote halogen or $C_1$–$C_6$-halogenoalkyl, halogen may for example be fluorine, chlorine or bromine, and $C_1$–$C_6$-halogenoalkyl may for example be $C_1$–$C_6$-halogenoalkyl containing 1 to 3 fluorine, chlorine and/or bromine atoms.

$R^1$ preferably represents hydrogen, methyl, ethyl, chlorine, methoxy or ethoxy. $R^2$ and $R^3$ preferably represent hydrogen. $R^4$ preferably represents hydrogen, methyl, ethyl or phenyl. Y preferably represents methyl, ethyl, phenyl, t-butyloxy, benzyloxy or menthyloxy. X preferably represents chlorine.

The preparation of compounds of the formula (I) is known from the literature (see for example Tetrahedron 50, 3889 (1994)) or can be carried out in analogy thereto.

Carbenes of type FXC: can be prepared, for example, in situ from dichloro- or dibromo-fluoromethane and alkyllithium at low temperatures (see Chem. Ber. 104, 1921 (1971)), from dichloro- or dibromo-fluoromethanes and an oxirane in the presence of tetraalkyl-, -aryl or -aralkyl-ammonium bromide (see Chem. Ber. 100, 1858 (1967)), from dichloro- or dibromo-fluoromethane with sodium hydroxide solution in the presence of a phase transfer catalyst (see J. Fluorine Chem. 49, 127 (1990)), or by reacting sodium methylate with methyl dichlorofluoroacetate (see Tetrahedron Letters 1967, 1123).

In a preferred procedure a mixture is prepared comprising a compound of the formula (I), aqueous sodium hydroxide solution, an inert, water-immiscible solvent and a phase transfer catalyst and dichlorofluoromethane is passed in at from −20° to +50° C., preferably −10° to +30° C., or dibromofluoromethane is added dropwise at from 0° to 40° C.

The aqueous sodium hydroxide solution may have, for example, a concentration of from 30 to 55% by weight, preferably from 45 to 50% by weight. Based on 100 g of the compound of the formula (I) it is possible, for example, to employ from 50 to 1000 ml of aqueous sodium hydroxide solution. This quantity is preferably from 80 to 600 ml.

A suitable inert, water-immiscible solvent is for example methylene chloride, toluene, chlorobenzene or trichlorotrifluoroethane. Dichloromethane is preferred. Based on 100 g of the compound of the formula (I) it is possible, for example, to employ from 40 to 800 ml of the solvent. This quantity is preferably from 70 to 700 ml.

Dichlorofluoromethane (R21) is a commercially available, industrial gas. Dibromofluoromethane can be obtained, for example, in accordance with Chem. Ber. 104, 1934–1941 (1971). Based on 1 mol of the compound of the formula (I) it is possible, for example, to employ from 1 to 10 mol of dichloro- or dibromo-fluoromethane. This quantity is preferably from 1 to 5 mol.

Examples of suitable phase transfer catalysts are quaternary ammonium salts such as benzyltriethylammonium chloride and tetrabutylammonium bromide, or crown ethers such as 18-crown-6 and dicyclohexano-18-crown-6, or quaternary phosphonium salts. Phase transfer catalysts can be employed, for example, in quantities of from 0.1 to 10 mol %, preferably from 0.5 to 8 mol %, based on the compound of formula (I).

The pressure during the reaction with the carbene, which is preferably formed in situ, is not critical. It may, for example, lie within the range from 0.1 to 40 bar. Atmospheric pressure and pressures of from 1 to 6 bar are preferred.

The mixture resulting from the reaction with the carbene can be worked up, for example, by diluting it with water or ice, extracting this mixture with an inert, water-immiscible solvent, preferably dichloromethane, drying the extract and finally removing the solvent, preferably in vacuum. In this way, the cyclopropylamine derivative of formula (II) is obtained which corresponds to the compound of the formula (I) employed and to the carbene-used.

The cyclopropylamine derivative of the formula (II) is then subjected to a reduction in which the substituent X is replaced by hydrogen. The reduction can be carried out, for example, with tributyltin hydride in the presence of a free-radical initiator, such as azoisobutyronitrile. Other possible reducing agents are sodium borohydride/tributyltin chloride, organosilicone hydrides in the presence of a free-radical initiator, and calcium/ammonia. The reduction can also be carried out electrochemically, and with hydrogen in the presence of Raney nickel, optionally in the presence of a base. Cyclopropylamine derivatives of the formula (II) where X=bromine can also be reduced with zinc.

It is advantageous to employ the reducing agent in excess. The temperature during the reduction can be selected at different levels depending on the reducing agent used. It should not be so high that the aromatic or cyclopropyl ring of the compound of the formula (II) is attacked. It is therefore usual to keep the temperature below 170° C., preferably below 150° C. The preferred temperatures are in the range from 70° to 120° C. when using hydrides, from 10° to 60° C. when using zinc, from 0° to 50° C. when carrying out electrochemical reduction, and from −40° to −20° C. when using calcium/ammonia. It is particularly preferred to operate with tributyltin hydride and azoisobutyronitrile at from 70° to 100° C. It is expedient to remove excess reducing agent after the end of the reduction, for example by distillation when using hydrides, or by aqueous work-up and extraction of the reaction product with an organic solvent when using calcium/ammonia or zinc.

The elimination of the COY group, which is currently still on the nitrogen atom, and of the substituted or unsubstituted benzyl group can be carried out in a manner known per se, for example by methods as described in Tetrahedron 50, 3889–3904 (1994) and Japanese Offenlegungsschrift (Japanese published application) 06-092 911.

The process according to the invention permits the preparation of 2-fluorocyclopropylamine in good yields, without auxiliaries which are difficult to handle or very resource-intensive to obtain. Moreover, the technical procedure is substantially more simple than is the case with previously known processes. The discovery of the process according to the invention was particularly surprising since, employing N-vinylphthalimide instead of a compound of the formula (I) and otherwise identical reaction conditions, no reaction took place (see Example 1). Moreover, when optically active compounds of the formula (I) are used, i.e. those where $R^4$ ≠hydrogen, no racemization takes place.

The cyclopropylamine derivatives of the formula (II) which are a key product in the process according to the invention for the preparation of 2-fluorocyclopropylamine are novel. The present invention therefore also relates to novel cyclopropylamine derivatives of the formula

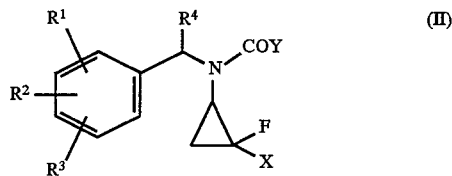

in which $R^1$, $R^2$ and independently of one another in each case represent hydrogen, $C_1$–$C_6$-alkyl, halogen, $C_1$–$C_6$-halogenoalkyl or $C_6$–$C_6$-alkoxy, $R^4$ represents hydrogen, $C_1$–$C_6$-alkyl or $C_6$–$C_{12}$-aryl, and Y represents open-chain or cyclic $C_1$–$C_{12}$-alkoxy, $C_6$–$C_{12}$-aryl, $C_7$–$C_{12}$-aralkyl, $C_7$–$C_{12}$-aralkyloxy or open-chain or cyclic $C_1$–$C_{12}$-alkyl, and X represents chlorine or bromine.

Preferred cyclopropylamine derivatives of the formula (II) are those in which $R^1$ represents hydrogen, methyl, ethyl, chlorine, methoxy or ethoxy, $R^2$ and $R^3$ represent hydrogen, $R^4$ represents hydrogen, methyl, ethyl or phenyl, Y represents methyl, ethyl, phenyl, t-butoxy, benzyloxy or menthyloxy and X represents chlorine.

Particularly preferred cyclopropylamine derivatives of the formula (II) are N-benzyl-N-(2-chloro-2-fluorocyclopropyl)- benzylcarbamate, N-benzyl-N-(2-bromo-2-fluorocyclo-propyl)-carbamate, N-benzyl-N-cis-and-trans(2-chloro-2-fluorocyclopropyl)-acetamide, N-(R)-α-methylbenzyl-N-(2-chloro-2-fluorocyclopropyl)-benzylcarbamate, N-(R)-α-methylbenzyl-N-(2-bromo-2-fluorocyclopropyl)-benzylcarbamate cyclopropyl)-benzylcarbamate and N-benzyl-N-(2-bromo-2-fluorocyclopropyl)-(1R, 2S, 5R)-p-menthylcarbamate.

A process for the preparation of cyclopropylamine derivatives of the formula (II) and their use for the advantageous preparation of 2-fluorocyclopropylamine have been described earlier above.

EXAMPLES

Example 1

(for comparison)

18 g of N-vinylphthalimide dissolved in 30 ml of methylene chloride were added dropwise at 0° C. to 30 g of 45% strength by weight sodium hydroxide solution. After addition of 1 g of benzyltriethylammonium chloride, 40 g of dichlorofluoromethane were passed in slowly at 0° to 5° C. After the end of the reaction, the mixture was poured onto ice, the organic phase was separated off and the aqueous phase was extracted with methylene chloride. After drying of the combined organic phases and removal of the solvent, spectroscopic analysis by GC-MS revealed no reaction product of the N-vinylphthalimide.

Example 2

41 g of dichlorofluoromethane were metered at from 5° to 10° C. over the course of 2 h into a mixture of 50 g of N-benzyl-N-vinylbenzylcarbamate, 80 ml of 45% strength aqueous sodium hydroxide solution, 50 ml of methylene chloride and 0.5 g of benzyltriethylammonium chloride. The mixture was subsequently diluted with water and extracted with methylene chloride. The extract was dried over sodium sulphate, and the solvent was removed from it under vacuum. The conversion was complete according to GC-MS, and 37 g of N-benzyl-N-(2-chloro-2-fluorocyclopropyl)-benzylcarbamate were obtained (yield= 59% of theory).

The $^1$H-NMR spectrum in deuterochloroform showed characteristic resonances at δ: 1.3–1.9 (m, 2H), 2.9 and 3.15 (m, 1H), 4.2–4.9 (m, 2H), 5.22 (s, 2H) and 7.1–7.5 (m, 10H) ppm.

The $^{19}$F-NMR spectrum in deuterochloroform showed characteristic resonances at δ: −137 and −152 ppm.

Example 3

21 g of dibromofluoromethane were added dropwise at from 5° to 10° C. over the course of 1.5 hours to a mixture of 24 g of N-benzyl-N-vinylbenzylcarbamate, 70 ml of 45% strength by weight aqueous sodium hydroxide solution, 60 ml of methylene chloride and 1 g of benzyltriethylammonium chloride. The mixture was subsequently diluted with water and extracted with methylene chloride. The extract was dried over sodium sulphate and then the solvent was removed under vacuum. 25.8 g of N-benzyl-N-(2-bromo-2-fluorocyclopropyl)-benzylcarbamate were isolated (yield: 75% of theory).

The $^1$H-NMR spectrum in deuterochloroform showed characteristic resonances at δ: 1.4–1.95 (m, 2H), 2.9 and 3.15 (m, 1H), 4.2–4.9 (m, 2H), 5.2 (s, 2H) and 7.1–7.5 (m, 10H) ppm.

The $^{19}$F-NMR spectrum in deuterochloroform showed characteristic resonances at δ: −134.5 and −150.5 ppm.

Example 4

83 g of dichlorofluoromethane were metered at from 5° to 10° C. over the course of 2 hours into a mixture of 100 g of N-benzyl-N-vinylacetamide, 400 ml of 45% strength by weight aqueous sodium hydroxide solution, 400 ml of methylene chloride and 4 g of benzyltriethylammonium chloride. The mixture was subsequently diluted with water and extracted with methylene chloride. The extract was dried over sodium sulphate and then the solvent was removed under vacuum. Following a conversion of 50% (determined by GC), there remained a cis/trans isomer mixture (ratio 1:2) of N-benzyl-N-cis-(2-chloro-2-fluorocyclopropyl)-acetamide and N-benzyl-N-trans-(2-chloro-2-fluorocyclopropyl)-acetamide.

The $^{19}$F-NMR spectrum in deuterochloroform showed characteristic resonances at δ: −136.4 and −149.7 ppm.

Example 5

95 g of dichlorofluoromethane were passed at from 5° to 10° C. over the course of 3 hours into a mixture of 95 g of N-(R)-α-methylbenzyl-N-vinylbenzylcarbamate, 100 ml of 45% strength by weight sodium hydroxide solution, 100 ml of methylene chloride and 2 g of benzyltriethylammonium chloride. The mixture was subsequently diluted with water and extracted with methylene chloride. The extract was dried over sodium sulphate and then the solvent was removed under vacuum. Yield: 54% (determined by NMR) of N (R)-α-methylbenzyl-N-(2-chloro-2-fluorocyclopropyl)-benzylcarbamate.

The $^1$H-NMR spectrum in deuterochloroform showed characteristic resonances at δ: 1.3–1.7 (m, 2H), 1,7 (t, 3H), 2.75–3.3 (m, 1H), 5.1–5.5 (m, 3H) and 7.2–7.5 (m, 10H) ppm.

The $^{19}$F-NMR spectrum in deuterochloroform showed characteristic resonances at δ: −138.3 and −150.6 ppm.

Example 6

48 g of dibromofluoromethane were added dropwise at from 5° to 10° C. over the course of 2 hours to a mixture of 56 g of N-(R)-α-methylbenzyl-N-vinylbenzylcarbamate, 55 ml of 45% strength by weight aqueous sodium hydroxide solution, 60 ml of methylene chloride and 1 g of benzyltriethylammonium chloride. The mixture was subsequently diluted with water and extracted with methylene chloride. The extract was dried over sodium sulphate and the solvent was removed under vacuum. Yield: 57% (determined by NMR) of N-(R)-α-methylbenzyl-(2-bromo-2-fluorocyclopropyl)-benzylcarbamate.

The $^1$H-NMR spectrum in deuterochloroform showed characteristic resonances at δ: 1.4–1.95 (m, 2H), 1.76 (t, 3H), 2.9–3.2 (m, 1H), 5.1–5.5 (m, 3H) and 7.2–7.5 (m, 10H) ppm.

The $^{19}$F-NMR spectrum in deuterochloroform showed characteristic resonances at δ: −136 and −149.9 ppm.

Example 7

81 g of dichlorofluoromethane were passed at from 5° to 10° C. over the course of 2 hours into a mixture of 50 g of N-benzyl-N-vinyl(1R, 2S, 5R)-p-menthylcarbamate, 80 ml of 45% strength by weight aqueous sodium hydroxide solution, 100 ml of methylene chloride and 2 g of benzyltriethylammonium chloride. The mixture was subsequently diluted with water and extracted with methylene chloride. The extract was dried over sodium sulphate and then the solvent was removed under vacuum. Yield: 70% (determined by NMR) of N-benzyl-N-(2-bromo-2-fluorocyclopropyl)-(1R, 2S, 5R)-p-menthyl-carbamate.

The $^1$H-NMR spectrum in deuterochloroform showed characteristic resonances at δ: 0.7–2.2, 2.7–3.3, 4.25, 4.6–4.9 and 7.3 ppm.

The $^{19}$F-NMR spectrum in deuterochloroform showed characteristic resonances at δ: −137 and −152 ppm.

Example 8

10 g of N-(R)-α-methylbenzyl-N-(2-chloro-2-fluorocyclopropyl)-benzylcarbamate, 9.2 g of tributyltin hydride and 0.3 g of azoisobutyronitrile (AIBN) were heated to 80°–90° C. The mixture was then stirred at from 80° to 90° C., for 4 hours, and a further 0.3 g of AIBN was added. After stirring for a further 4 hours, the reaction mixture was cooled and separated by column chromatography on silica gel (n-hexane/MTBE 5:1). Yield: 2.8 g (=32%) of trans-N-(R)-α-methylbenzyl-N-(2-fluorocyclopropyl)-benzylcarbamate and 2.73 g (31%) of cis-N-(R)-α-methylbenzyl-N-(2-fluorocyclo-propyl)-benzylcarbamate, i.e. a total of 63%. The physical data corresponded to the literature values.

Example 9

The products of Example 8 were subjected separately to hydrogenation in order to eliminate the benzyl group and to an acidic elimination of the carbamate group in the manner described in Tetrahedron 50, 3889–3904 (1994), to give in both cases 2-fluorocyclopropylamine in the yields indicated therein.

What is claimed is:

1. Cyclopropylamine derivatives of the formula

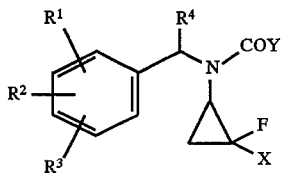

(II)

in which

R$^1$, R$^2$ and R$^3$ independently of one another in each case represent hydrogen, C$_1$–C$_6$-alkyl, halogen, C$_1$–C$_6$-halogenoalkyl or C$_1$–C$_6$-alkoxy, R$^4$ represents hydrogen, C$_1$–C$_6$-alkyl or C$_6$–C$_{12}$-aryl, and Y represents open-chain or cyclic C$_1$–C$_{12}$-alkoxy, C$_6$–C$_{12}$-aryl, C$_7$–C$_{12}$-aralkyl, C$_7$–C$_{12}$-aralkyloxy or open-chain or cyclic C$_1$–C$_{12}$-alkyl, and X represents chlorine or bromine.

2. Cyclopropylamine derivatives of claim 1, in which

R$^1$ represents hydrogen, methyl, ethyl, chlorine, methoxy or ethoxy,

R$^2$ and R$^3$ represent hydrogen,

R$^4$ represents hydrogen, methyl, ethyl or phenyl,

Y represents methyl, ethyl, phenyl, t-butyloxy, benzyloxy or menthyloxy and

X represents chlorine.

3. Cyclopropylamine derivatives of claim 1, which are N-benzyl-N-(2-chloro-2-fluorocyclopropyl)-benzylcarbamate, N-benzyl-N-(2-bromo-2-fluorocyclopropyl)-carbamate, N-benzyl-N-cis- and -trans (2-chloro-2-fluorocyclopropyl)-acetamide, N-(R)-α-methylbenzyl-N-(2-chloro-2-fluorocyclopropyl)-benzylcarbamate, N-(R)-α-methylbenzyl-N-(2-bromo-2-fluorocyclopropyl)-benzylcarbamate and N-benzyl-N-(2-bromo-2-fluorocyclopropyl)-(1R, 2S, 5R)-p-menthylcarbamate.

* * * * *